United States Patent [19]

Niijima et al.

[11] Patent Number: 5,362,365
[45] Date of Patent: Nov. 8, 1994

[54] PURIFICATION OF ACETIC ANHYDRIDE OR ACETIC ANHYDRIDE AND ACETIC ACID USING OZONE

[75] Inventors: Hiroyuki Niijima; Kazuyuki Akita, both of Himeji, Japan

[73] Assignee: Daicel Chemical Industries, Ltd., Sakai, Japan

[21] Appl. No.: 88,035

[22] Filed: Jul. 6, 1993

[30] Foreign Application Priority Data

Jul. 7, 1992 [JP] Japan ................... 4-179903

[51] Int. Cl.$^5$ ............... B01D 3/34; C07C 51/42; C07C 51/573
[52] U.S. Cl. ................ 203/31; 203/98; 203/DIG. 19; 562/519; 562/608; 562/891; 562/898
[58] Field of Search .............. 203/31, 98, DIG. 19, 203/DIG. 12; 562/608, 519, 607, 890, 891, 898

[56] References Cited

U.S. PATENT DOCUMENTS

| 2,255,421 | 9/1941 | Groll et al. | 203/31 |
|---|---|---|---|
| 2,278,831 | 4/1942 | Cockerille | 203/31 |
| 2,893,923 | 7/1959 | Luke et al. | 203/31 |
| 3,928,434 | 12/1975 | Saunby | 562/608 |
| 4,664,753 | 5/1987 | Erpenbach et al. | 562/608 |
| 5,155,265 | 10/1992 | Scates et al. | 562/608 |
| 5,155,266 | 10/1992 | Scates et al. | 562/608 |
| 5,202,481 | 4/1993 | Scates et al. | 562/608 |

FOREIGN PATENT DOCUMENTS

| 0322215 | 6/1989 | European Pat. Off. |
| 48-030615 | 9/1973 | Japan |
| 5564545 | 11/1978 | Japan |
| 60-222439 | 4/1984 | Japan |
| 61-002052 | 1/1986 | Japan |
| 61-056151 | 3/1986 | Japan |
| 01211548 | 8/1989 | Japan |
| 02231448 | 9/1990 | Japan |

*Primary Examiner*—Wilbur Bascomb, Jr.
*Attorney, Agent, or Firm*—Cushman, Darby & Cushman

[57] ABSTRACT

Acetic acid and/or acetic anhydride containing methyl crotonate, vinyl acetate, or both as impurities, is contacted with ozone in an amount of excess molar to the carbon-carbon double bond in said methyl crotonate and/or vinyl acetate and the impurities produced by ozone-treatment are removed off by distillation. A large quantity of impurities such as aldehydes are produced after treatment by treating acetic acid and/or acetic anhydride containing much amount of unsaturated compounds as impurities with ozone. Distilling the ozone-treated acetic acid and/or acetic anhydride make it possible to remove methyl crotonate and vinyl acetate, which are unsaturated compounds difficult to remove by the conventional separation methods, to give high-quality acetic acid and/or acetic anhydride excellent in the residence time in the potassium permanganate test.

17 Claims, No Drawings

PURIFICATION OF ACETIC ANHYDRIDE OR ACETIC ANHYDRIDE AND ACETIC ACID USING OZONE

FIELD OF THE INVENTION

The present invention relates to a method of purifying acetic acid and/or acetic anhydride and, more particularly, to a method of purifying acetic acid and/or acetic anhydride produced by catalytic carbonylation of (1) methanol and/or methyl acetate or (2) methanol and/or dimethyl ether.

BACKGROUND OF THE INVENTION

Several methods are known for commercial production of acetic acid, which comprise, for example, (a) oxidizing acetaldehyde, (b) directly oxidizing petroleum naphtha, butane, propane or the like, (c) purifying acetic acid obtained as a byproduct in the synthesis of epoxides from olefins and peracetic acid or from unsaturated alcohols and peracetic acid, or (d) contacting methanol with carbon monoxide for carbonylation in the presence of a transition metal catalyst such as rhodium and a halogen-containing organic promoter such as methyl iodide.

Methods known for commercial production of acetic anhydride comprise, for example, (e) reacting acetic acid with ketene prepared by pyrolysis of acetic acid, or (f) contacting methyl acetate or dimethyl ether with carbon monoxide for carbonylation in the presence of a transition metal catalyst such as rhodium and a halogen-containing organic promoter such as methyl iodide.

In particular, the method of producing acetic acid or acetic anhydride by carbonylation with carbon monoxide is a very advantageous commercial production method. As another convenient method, there may be mentioned the method of producing acetic acid and acetic anhydride simultaneously which comprises reacting methyl acetate and methanol, or dimethyl ether and methanol, with carbon monoxide.

Generally, however, the product acetic acid or acetic anhydride obtained by such methods as mentioned above contains such impurities as reducing substances, carbonylation products, and halogen compounds. These impurities exert a very serious influence on the result of the potassium permanganate test (commonly known as chameleon test), which is an important index of the quality of acetic acid and acetic anhydride. It is therefore necessary to remove such impurities from the product acetic acid and product acetic anhydride to a great and satisfactory extent.

As other means for removing said impurities than the distillation method which requires a high degree of energy consumption, there are known treatment methods which use ozone, peracetic acid or hydrogen.

Thus, the method disclosed in Japanese Patent laid open No. (JP-A) 02-231448, which uses hydrogen, comprises treating impurity-containing acetic acid with hydrogen at a temperature of about 17° to 200° C. and a hydrogen pressure of about 1 to 30 atmospheres in the presence of 0.01 to 10% by weight of a hydrogenation catalyst and then recovering acetic acid.

The method disclosed in Japanese Patent Publication No.(JP-B) 48-30615, which uses peracetic acid, comprises adding peracetic acid to acetic acid showing a short residence time in the potassium permanganate test and subjecting the resulting mixture to distillation for purification, to give acetic acid of improved quality. Japanese Patent laid open No.(JP-A) 61-56151 discloses a method of preparing acetic acid of improved quality which comprises adding peracetic acid to acetic acid showing a short residence time in the potassium permanganate test, treating the mixture by heating at a temperature within the range of 50° to 120° C. and subjecting the same to distillation for purification.

As for the methods which use ozone, Japanese Patent laid open No.(JP-A) 60-222439 discloses a method comprising treating crude acetic anhydride with an ozone-containing gas. Japanese Patent Publication No.(JP-B) 61-2052 discloses a method of producing acetic acid improved in residence time in the potassium permanganate test which comprises treating acetic acid with a purity of not less than 99% with an ozone-containing gas in the absence of any catalyst metal compound. Further, Japanese Patent laid open No.(JP-A) 01-211548 corresponding to U.S. Ser. No. 137,844, now abandoned, discloses a method comprising contacting acetic acid containing halides, unsaturated compounds and carbonyl compounds as impurities with a sufficient amount of ozone to oxidize said impurities in the presence or absence of a catalyst and recovering purified acetic acid.

Among these treatment methods, those which use ozone or an ozone-containing gas are estimated to be most advantageous from the viewpoints of economy and safety, among others, and are in practical use for the production of acetic acid and acetic anhydride. They are particularly effective in treating impurities close in boiling point to acetic acid or acetic anhydride, hence difficult to remove to a satisfactory extent by distillation.

When, however, unsaturated compounds as impurities are present in an amount of the order several hundred to several thousand parts per million (ppm), no substantial improvement in residence time in the potassium permanganate test will be produced in some cases because of influences of products formed from the impurities upon ozone treatment, although ozone treatment alone can give acetic acid or acetic anhydride of good quality with a long residence time in the potassium permanganate test when unsaturated compounds are present only in trace amounts.

SUMMARY OF THE INVENTION

Accordingly, it is an object of the invention to clear up the causes of such cases and thereby provide a method of purifying acetic acid and/or acetic anhydride which is simple and easy to perform and has the advantage of the ozone treatment method mentioned above.

It is another object of the invention to provide a method of purifying acetic acid and/or acetic anhydride to a high degree in a simple and easy manner even when unsaturated compounds are present in fairly large amounts.

A further object of the invention is to provide a method of efficiently and highly purifying acetic acid and acetic anhydride produced by a method capable of producing them simultaneously.

The present inventors made intensive investigations on the problems mentioned above and, as a result, found that there are vinyl acetate and methyl crotonate present as particularly trouble-making unsaturated compounds. Among them, methyl crotonate, which is found particularly in large amounts when acetic acid and acetic anhydride are produced simultaneously by reacting methyl acetate and methanol, or dimethyl ether and methanol, with carbon monoxide, has a boiling point substantially identical to that of acetic acid and is therefore very difficult to remove by ordinary distillation. Further, it was revealed that when treated with ozone, these unsaturated compounds give acetaldehyde, which is a substance exerting an aggravating influence on the residence time in the potassium permanganate test.

Paying attention to the fact that the ozone treatment product acetaldehyde differs markedly in boiling point from acetic acid and/or acetic anhydride, conducted intensive investigations in an attempt to develop a process for purifying acetic acid and/or acetic anhydride containing vinyl acetate and methyl crotonate as impurities by combining ozone treatment and separation by distillation and, as a result, found out an optimal process. They have thus completed the present invention.

The invention thus provides a method of purifying acetic acid and/or acetic anhydride containing methyl crotonate or vinyl acetate, or both as impurities which comprises contacting said acetic acid and/or acetic anhydride with ozone and the subjecting the same to distillation.

Ozone is used generally in an amount at least equimolar to the carbon-carbon double bond in methyl crotonate and vinyl acetate. The ozone-treated acetic acid and/or acetic anhydride is fed to a distillation column (a distillation tower), where purified acetic acid and/or acetic anhydride is separated from impurities formed upon ozone treatment.

DETAILED DESCRIPTION OF THE PREFERRED EMBODIMENT OF THE INVENTION

The present invention is applicable to any grade of acetic acid or acetic anhydride, or a mixture of these that contains vinyl acetate or methyl crotonate, or both. The purification method of the invention may be preferably applied to any grade of acetic acid and/or acetic anhydride produced, in the presence of a catalytic system, by carbonylation of (1) methanol and/or methyl acetate or (2) methanol and/or dimethyl ether.

The catalytic system, usually, comprises a transition metal component (e.g. Ru, Rh, Pd, Os, Ir, Pt, etc.), and an alkyl halide as a co-catalyst. Among transition metal components, a rhodium component is preferred to give an excellent activity. Examples of the rhodium component include rhodium, rhodium salts such as rhodium halide and hydrate thereof, a salt of rhodium with an organic acid such as rhodium acetate, etc., and a coordination compound of rhodium such as a rhodium carbonyl compound, a halogeno rhodium carbonyl compound, etc. The alkyl halide includes, for example, methyl iodide, methyl bromide and the like. The preferred catalytic system contains the rhodium component and methyl iodide.

The rhodium component may be utilized in a proportion of, for example, 0.1 to 50 mmol per liter, preferably about 1 to 30 mmol per liter. The proportion of the alkyl halide may be 0.1 to 10 mol per liter, preferably about 1 to 5 mol per liter.

The catalytic system may contain the third component. As examples of the third component, there may be mentioned an alkali metal iodide (for example, lithium iodide, sodium iodide, potassium iodide and so on), an alkali metal (e.g. lithium, sodium, etc.), a stabilizer for the catalyst (for example, aluminium and a compound thereof, boron and a compound thereof, a phosphonium salt, a nitrogen-containing compound and a salt thereof, a phosphorus compound, etc.) and so on. These components may be employed singly or in combination. The preferred examples of the third component include an alkali metal iodide, and especially preferred is lithium iodide. The third component is utilized in a proportion of, for example, about 0.1 to 5 mol per liter.

In the carbonylation reaction, methanol is reacted with carbon monoxide to give acetic acid and methyl acetate, and methyl acetate is reacted with carbon monoxide to give acetic anhydride. Dimethyl ether is, similarly, converted into acetic anhydride by carbonylation. Further, acetic anhydride is converted into acetic acid in the presence of water. Accordingly, (1) acetic acid and/or acetic anhydride can be produced by reacting methanol and/or methyl acetate with carbon monoxide, if necessary, in the presence of water. Similarly, (2) acetic acid and/or acetic anhydride can also be produced by reacting methanol and/or dimethyl ether with carbon monoxide.

When both methanol and methyl acetate, or methanol and dimethyl ether, are reacted with carbon monoxide, the amount of methanol to be charged may be selected from a wide range, for example, about 0.1 to 10 times, on the molar basis, as compared with the amount of methyl acetate or dimethyl ether.

In order to prevent production of by-products such as methane and the like, it is useful, for example, to introduce hydrogen into the reaction system in a concentration of about 1 to 20% by volume.

The reaction is carried out at 130° C. to 250° C., preferably at about 150° C. to 200° C., while the partial pressure of carbon monoxide is 1 to 100 kg/cm$^2$G, preferably about 5 to 50 kg/cm$^2$G.

The reaction can be conducted in the presence or absence of water. The concentration of water ranges, for example, from 0 to 15 mol per liter, preferably from about 0 to 10 mol per liter. Where the carbonylation reaction is conducted in a reaction system with a high water concentration, the proportion of acetic acid to the products increases. To the contrary, in a system with a low water concentration, the proportion of acetic anhydride increases. A large quantity of energy is required to remove water from resulting products when the reaction is carried out in a system containing much amount of water. Hence, the preferred concentration of water is 0 to 5 mol per liter, preferably about 0 to 3 mol per liter.

When the carbonylation is carried out in a reaction system with a low water concentration, in particular in the absence of water, vinyl acetate and methyl crotonate are formed in increased amounts and the product acetic acid and acetic anhydride formed show a short residence time in the potassium permanganate test. The present invention is preferably applied to the purification of acetic acid and acetic anhydride produced by such method, in particular to the purification of acetic acid and acetic anhydride produced by reacting methanol and methyl acetate with carbon monoxide.

The method of preparing ozone or an ozone-containing gas for use in the practice of the invention is not limited to any specific one. For commercial purposes, however, ozone is generally generated by such technique as silent discharge, corona discharge or ultraviolet irradiation using air or oxygen as a starting material. Generally, ozone is generated by silent discharge in most cases. The starting material may be either air or oxygen. In cases where the unsaturated compound content is high, hence a large amount of ozone is required for the treatment, oxygen is preferred as the starting material from the viewpoints of energy cost and prevention of airing loss of acetic acid and/or acetic anhydride, since the ozone concentration in the treating gas can be increased.

The reactor for the ozone treatment is not limited to any particular type, either, provided that good contact can be ensured between ozone and acetic acid and/or acetic anhydride. For practical purposes, the impeller-equipped stirring vessel type and sparger-equipped bubble column type are preferred.

The time of contact with ozone may depend on the reaction conditions. Generally, however, the reaction between ozone and methyl crotonate and/or vinyl acetate can proceed rapidly even in the absence of any catalyst or the like. Thus, generally, the contact time can be suitably be selected in the range of several minutes to scores of minutes (e.g. 1 to 30 minutes, preferably about 1 to 15 minutes) expressed in terms of average contact time.

The reaction temperature is, for instance, 10° C. to 50° C., preferably around room temperature. A preferred reaction temperature is in the range of about 20° C. to 35° C. The upper temperature limit can be determined such that the off-gas composition will not enter the explosion range. Excessively low temperatures are unfavorable because of decreased rate of reaction while excessively high temperature are unfavorable as well because of the tendency of ozone toward self-decomposition.

Although ozone can react almost quantitatively with the carbon-carbon double bond in the impurity methyl crotonate and/or vinyl acetate, there is the possibility of decomposition of ozone itself, for instance. Therefore, it is recommended that ozone to be contacted with acetic acid and/or acetic anhydride be charged in slight excess so that the reaction can be driven to completion. When the economical aspect is also taken into consideration, a preferred amount of ozone to be charged is about 1.1 to 2 times, preferably about 1.1 to 1.7 times, on the molar basis, as compared with the carbon-carbon double bond in methyl crotonate and/or vinyl acetate.

The amount of ozone can generally be selected according to the content of impurities in acetic acid and/or acetic anhydride and is, for example, about 1 to 1,000 ppm, preferably about 5 to 500 ppm, relative to acetic acid and/or acetic anhydride.

The new impurities formed upon ozone treatment can be removed by distillation, preferably by rectification.

The type of the distillation column is not critical but can suitably be selected by one skilled in the art. Generally, one or more can be selected from among plate columns such as sieve tray columns, bubble cap tray columns and bubble tray columns, and packed columns such as columns packed with Intalox saddles, columns packed with Pall rings and columns with Sulzer packings.

Plate columns containing about 20 to 80 trays, preferably about 25 to 80 trays, and packed columns with a corresponding packing height are preferred. The number of trays or the packing height and the column diameter can be optimized depending on the rate of flow of acetic acid and/or acetic anhydride to be purified and the contents of formaldehyde and acetaldehyde to be removed.

The acetic acid and/or acetic anhydride to be purified is introduced into the middle section, or an upper part thereof, of the distillation column. The site of introduction is higher than the site of recover of the product acetic acid and/or acetic anhydride. Desirably, a site higher than the middle of the distillation column is selected.

The product acetic acid and/or acetic anhydride is recovered in the form of a vapor or liquid from below the raw material introduction site, desirably from a site lower than the middle of the distillation column.

From the viewpoint of removal of low-boiling impurities such as aldehydes, the site of recovery should desirably be as close to the bottom as possible. In some instances, however, high-boiling impurities such as aldehyde polymers may be present in the liquid phase in the lower part of the distillation column. Such high-boiling impurities should desirably be removed to attain an increased purity of acetic acid and/or acetic anhydride, although their influence on the residence time in the potassium permanganate test is not so great as that of the low-boiling impurities mentioned above. Therefore, when a plate column is used, the product is most desirably recovered in the form of a vapor from the 1st to 5th plate, preferably the 1st to 3rd plate, from the distillation column bottom.

The concentrated low-boiling components such as aldehydes is partly recovered from the overhead vapor condensate. The high-boiling fraction consisting of aldehyde polymers and others is recovered from the column bottom. The remainder of the overhead vapor condensate is returned to the column top as a reflux.

The height $H_i$, from the column bottom, of the site for introducing the ozone-treated raw material and the height $H_r$, from the column bottom, of the site for recovering the purified product, relative to the height of the distillation column $H_d$, respectively are preferably as follows:

$H_i/H_d$ = 50 to 80%, preferably about 55 to 75% and $H_r/H_d$ = 0 to 40%, preferably about 5 to 25%.

The ratio between the rate of flow of the recovered liquid and the rate of flow of the reflux (the so-called reflux ratio) should be determined according to the raw material liquid composition, the product quality required and other factors. Generally, however, said ratio can be selected in the range of about 1 to 1,000. When the aldehyde concentration in the raw material is about several hundred to several thousand ppm (for example, about 200 to 5,000 ppm), the reflux ratio is desirably within the range of 50 to 500, preferably about 100 to 300.

The operation pressure within the distillation column is not critical. However, an excessively high pressure may possibly result in an increase in the temperature within the column, leading to undesirable reactions such as polymerization of aldehydes. If, conversely, the pressure is too low, the condensation of the vapor at the column top becomes difficult. Therefore, the operation pressure at the column top is preferably in the range of 100 mmHg to atmospheric pressure, preferably 250 mmHg to atmospheric pressure.

The mere combination of ozone treatment and distillation according to the invention makes it possible to remove methyl crotonate and vinyl acetate, which are unsaturated compounds difficult to remove by the conventional separation methods, to give high-quality acetic acid and/or acetic anhydride excellent in the residence time in the potassium permanganate test.

The potassium permanganate test comprises adding 1 ml of 0.1N aqueous potassium permanganate to 50 ml of acetic acid and/or acetic anhydride, shaking the mixture, and measuring the time required for the purple color to change into a standard amber color. The time required for the above discoloration corresponds to the content of impurities in the sample; the higher the impurity content is, the shorter the time required for the discoloration is.

The following examples and reference examples illustrate the invention in further detail. They are, however, by no means limitative of the scope of the invention.

EXAMPLES

Comparative Example 1

To 10.5 kg of acetic acid showing a residence time of not less than 240 minutes in the potassium permanganate test was added 10.5 g (1,000 ppm based on the acetic acid) of methyl crotonate, and the mixture was charged into a reactor equipped with a stirrer. Batchwise treatment was conducted, at 30° C., by passing air containing 16 g/Nm$^3$ of ozone through the charge via a sparger at a rate of 150 Nl/hr for 3.2 hours. The amount of ozone contacted with the charge was 1.5 times, on the molar basis, the methyl crotonate contained in the charge.

The content of methyl crotonate in the treated acetic acid was below 0.5 ppm (detection limit in the analysis) while said acetic acid was found to contain 246 ppm of acetaldehyde. The acetic acid after treatment showed a residence time of 0 minute in the potassium permanganate test.

Example 1

The acetic acid obtained after ozone treatment in Comparative Example 1 was continuously fed to the 13th plate, from the top, of a distillation column (40 mm in inside diameter, made of glass) containing 30 sieve trays at a rate of 400.0 g/hr. The column was operated in a reflux ratio of 200 and at a column top pressure of 1 atmosphere. The overhead liquid consisting of a concentrated low-boiling fraction was partly and continuously withdrawn at a rate of 2.0 g/hr, and the column bottom liquid consisting of purified acetic acid at a rate of 398.0 g/hr.

The acetic acid withdrawn from the bottom contained a high-boiling fraction, and the content of which was estimated at about 1 ppm. This acetic acid showed an improved residence time of 135 minutes in the potassium permanganate test.

Example 2

The acetic acid obtained after ozone treatment in Comparative Example 1 was continuously fed to the 13th plate, from the top, of a distillation column (40 mm in inside diameter, made of glass) containing 30 sieve trays at a rate of 400.0 g/hr while the column was operated in a reflux ratio of 200 and at a column top pressure of 1 atmosphere. The overhead liquid consisting of a concentrated low-boiling fraction was partly and continuously withdrawn at a rate of 2.0 g/hr and purified acetic acid as a vapor side cut from the 27th plate at a rate of 392.0 g/hr. Acetic acid containing a high-boiling fraction was continuously withdrawn from the bottom at a rate of 6.0 g/hr. The purified acetic acid from the 27th plate was found to be substantially free of impurities and showed an improved residence time of not less than 240 minutes in the potassium permanganate test.

Example 3

To 10.5 kg of acetic acid showing a residence time of not less than 240 minutes in the potassium permanganate test were added 10.5 g (1,000 ppm based on the acetic acid) of methyl crotonate and 15.8 g (1,500 ppm based on the acetic acid) of vinyl acetate, and the mixture was continuously fed, at a rate of 250.0 g/hr, to a complete mixing type bubble column (40 mm inside diameter, 1 m in height, made of glass, simple in structure without any baffle plate or the like, equipped with a sparger at the bottom) maintained at 30° C.

On the other hand, oxygen containing 120 g/Nm$^3$ of ozone was continuously introduced, simultaneously with the acetic acid mentioned above, into the above bubble column from the bottom thereof via said sparger at a rate of 3.3 Nl/hr. The amount of ozone introduced was 1.2 moles per mole of the methyl crotonate plus vinyl acetate contained in the charge.

The acetic acid continuously withdrawn from the complete mixing type bubble column was continuously fed, as such, to the 13th plate, from the top, of a distillation column (40 mm in inside diameter, made of glass) containing 40 sieve trays at a rate of 250.0 g/hr. The distillation column was continuously operated concurrently with the bubble column mentioned above in a reflux ratio of 200 and at a column top pressure of 500 mmHg. The overhead liquid consisting of a concentrated low-boiling fraction was partly and continuously withdrawn at a rate of 1.25 g/hr, and purified acetic acid as a vapor side cut from the 37th plate, from the top, at a rate of 245.0 g/hr. Acetic acid containing a high-boiling fraction was continuously withdrawn from the column bottom at a rate of 3.75 g/hr.

The purified acetic acid from the 37th plate was substantially free of impurities and showed a residence time of not less than 240 minutes in the potassium permanganate test.

Example 4

A catalytic solution containing 0.94% by weight of rhodium iodide (RhI$_3$), 7.8% by weight of lithium iodide, 45.6% by weigh of acetic acid and 45.6% by weight of acetic anhydride was continuously fed, at a rate of 7 kg/hr, to a reactor, and methyl acetate, methyl iodide and methanol at a rate of 6.6 kg/hr, 8.8 kg/hr and 5.6 kg/hr respectively. The reaction was conducted at 185° C. while a pressurized carbon monoxide under the pressure of 17 kg/cm$^2$G and a pressurized hydrogen gas under 2 kg/cm$^2$G were continuously charged to the reactor. The reaction mixture was continuously withdrawn from the reactor and fed to a flash evaporator maintained at 130° C. under 2.4 kg/cm$^2$G. In the flash evaporator, unevaporated fraction containing the catalytic system such as rhodium component and co-catalysts was fed back to the reactor, and acetic acid and acetic anhydride as products, methyl iodide as a catalytic component, unreacted methyl acetate and a slight amount of by-products were evaporated and fed to the first distillation column of a distillation system.

In the distillation system, methyl iodide and methyl acetate were continuously withdrawn from the column top of the first distillation column and fed back to the reactor, and acetic acid and acetic anhydride as a vapor side cut continuously fed to the second distillation column. Distillated acetic acid from the column top of the second distillation column and acetic anhydride as a vapor side cut were continuously withdrawn at a rate of 10.5 kg/hr respectively.

The distillated acetic acid containing 1,000 ppm of methyl crotonate was continuously fed, at a rate of 250.0 g/hr, to a complete mixing type bubble column (40 mm inside diameter, 1 m in height, made of glass, simple in structure without any baffle plate or the like, equipped with a sparger at the bottom) maintained at 30° C. On the other hand, oxygen containing 60 g/Nm$^3$ of ozone was continuously introduced, simultaneously with the acetic acid mentioned above, into the above bubble column from the bottom thereof via said sparger at a rate of 3.0 Nl/hr. The amount of ozone introduced was 1.5 moles per mole of the methyl crotonate contained in the charge.

The acetic acid continuously withdrawn from the complete mixing type bubble column was continuously fed to a distillation column (40 mm in inside diameter, made of glass) containing 40 sieve trays and distillation was conducted in the same manner as in Example 3.

The purified acetic acid thus obtained was free of methyl crotonate and showed a residence time of not less than 240 minutes in the potassium permanganate test.

The distillated acetic anhydride was treated with ozone and distillated in the same manner as above, and the purified acetic anhydride thus obtained was free of methyl crotonate and showed a residence time of not less than 240 minutes in the potassium permanganate test.

What is claimed is:

1. A method of purifying acetic anhydride or a mixture of acetic anhydride and acetic acid containing methyl crotonate, vinyl acetate, or both as impurities, wherein said acetic anhydride or said mixture of acetic anhydride and acetic acid is produced by reacting (1) dimethyl ether, (2) methyl acetate, (3) a mixture of dimethyl ether and methanol, (4) a mixture of methyl acetate and methanol, or (5) a mixture of dimethyl ether, methyl acetate, and methanol with carbon monoxide, which comprises contacting said acetic anhydride or said mixture of acetic anhydride and acetic acid with ozone and subjecting said ozone-treated acetic anhydride or said ozone-treated mixture of acetic anhydride and acetic acid to distillation.

2. A method of purifying acetic anhydride or a mixture of acetic anhydride and acetic acid as recited in claim 1, wherein ozone is used in an amount at least equimolar to the carbon-carbon double bond in said methyl crotonate, vinyl acetate, or both.

3. A method of purifying acetic anhydride or a mixture of acetic anhydride and acetic acid as recited in claim 1, wherein ozone is used in an amount 1.1 to 2 times the carbon-carbon double bond in said methyl crotonate, vinyl acetate, or both on a molar basis.

4. A method of purifying acetic anhydride or a mixture of acetic anhydride and acetic acid as recited in claim 1, wherein said acetic anhydride or said mixture of acetic anhydride and acetic acid to be purified is contacted with ozone to attain an average contact time of 1 to 30 minutes.

5. A method of purifying acetic anhydride or a mixture of acetic anhydride and acetic acid as recited in claim 1, wherein said acetic anhydride or said mixture of acetic anhydride and acetic acid to be purified is contacted with ozone at a temperature of 20° C. to 35° C.

6. A method of purifying acetic anhydride or a mixture of acetic anhydride and acetic acid as recited in claim 1, wherein said ozone-treated acetic anhydride or said ozone-treated mixture of acetic anhydride and acetic acid is introduced into a distillation column, having a top and a bottom and a middle section, at an introduction site located at said middle section of said distillation column or at an upper part of said middle section, and wherein a low-boiling impurity fraction is recovered from said top of said distillation column and purified acetic anhydride or a purified mixture of acetic anhydride and acetic acid in a vapor or liquid form is recovered at a recovery site located at said bottom of said distillation column or below said introduction site.

7. A method of purifying acetic anhydride or a mixture of acetic anhydride and acetic acid as recited in claim 6, wherein said distillation column has a height Hd, a height Hi measured from said bottom of said distillation column to said introduction site, and a height Hr measured from said bottom of said distillation column to said recovery site, and wherein the ratios: Hi/Hd=50% to 80% and Hr/Hd=0% to 40%.

8. A method of purifying acetic anhydride or a mixture of acetic anhydride and acetic acid as recited in claim 1, wherein said ozone-treated acetic anhydride or said ozone-treated mixture of acetic anhydride and acetic acid is introduced into a plate column, having a top and a bottom and a middle section, at an introduction site located at said middle section of said plate column or at an upper part of said middle section, wherein said plate column contains 20 to 80 plates and wherein a low-boiling impurity fraction is partly recovered from said top of said plate column, and wherein remaining overhead liquid is returned to said top of said plate column as a reflux, and wherein purified acetic anhydride or a purified mixture of acetic anhydride and acetic acid is recovered in a vapor form from said 1st to 5th plate from said bottom of said plate column, with a high-boiling impurity fraction being recovered from said bottom of said plate column.

9. A method of purifying acetic anhydride or a mixture of acetic anhydride and acetic acid as recited in claim 8, wherein said distillation is carried out in a reflux ratio of 50 to 500.

10. A method of purifying acetic anhydride or a mixture of acetic anhydride and acetic acid as recited in claim 6, wherein said distillation column is operated at a column top pressure of 100 mmHg to atmospheric pressure.

11. A method of purifying acetic anhydride or a mixture of acetic anhydride and acetic acid as recited in claim 1, wherein said reactions (1)-(5) are conducted in the presence of a rhodium component and a methyl halide.

12. A method of purifying acetic anhydride or a mixture of acetic anhydride and acetic acid as recited in claim 1, wherein said acetic anhydride or said mixture of acetic anhydride and acetic acid to be purified is contacted with ozone used in an amount, on a molar basis, 1.1 to 1.7 times the carbon-carbon double bond in said impurities at a temperature of 20° C. to 35° C. to attain an average contact time of 1 to 30 minutes and wherein said ozone-treated acetic anhydride or said ozone-treated mixture of acetic anhydride and acetic acid is introduced into a distillation column, having a top and a bottom and a middle section, at an introduction site located at said middle section of said distillation column or at an upper part of said middle section of said distillation column, a low-boiling impurity fraction being recovered from said top of said distillation column and purified acetic anhydride or a purified mixture of acetic anhydride and acetic acid being recovered in a vapor or liquid form from said bottom of said distillation column or a site below said introduction site.

13. A method of purifying acetic anhydride or a mixture of acetic anhydride and acetic acid as recited in claim 1, wherein said ozone-treated acetic anhydride or said ozone-treated mixture of acetic anhydride and acetic acid is introduced into a plate column, having a top and a bottom and a middle section, at an introduction site located at said middle section of said plate column or at an upper part of said middle section, wherein said plate column contains 20 to 80 plates, and wherein said plate column is operated at a column top pressure of 100 mmHg to atmospheric pressure, and wherein a low-boiling impurity fraction is partly recovered from said top of said plate column and remaining overhead liquid is returned as a reflux in a reflux ratio of 50 to 500, and wherein purified acetic anhydride or a purified mixture of acetic anhydride and acetic acid is recovered in a vapor form from said 1st to 5th plate from said bottom of said plate column, with a high-boiling impurity fraction being recovered from said bottom of said plate column.

14. A method of purifying acetic anhydride or a mixture of acetic anhydride and acetic acid containing methyl crotonate, vinyl acetate, or both as impurities, wherein said acetic anhydride or said mixture of acetic anhydride and acetic acid is produced by reacting (1) dimethyl ether, (2) methyl acetate, (3) a mixture of dimethyl ether and methanol, (4) a mixture of methyl acetate and methanol, or (5) a mixture of dimethyl ether, methyl acetate and methanol with carbon monoxide, which comprises the steps of:

contacting said acetic anhydride or said mixture of acetic anhydride and acetic acid with ozone;

introducing said ozone-treated acetic anhydride or said ozone-treated mixture of acetic anhydride and acetic acid into a plate column, having a top and a bottom and a middle section, at an introduction site located at said middle section of said plate column or at an upper part of said middle section;

recovering a low-boiling impurity fraction from said top of said plate column; and recovering purified acetic anhydride or purified mixture in a vapor or liquid form from a recovery site located at said bottom of said plate column or below said introduction site, wherein said plate column has a height Hd, a height Hi measured from said bottom of said plate column to said introduction site, and a height Hr measured from said bottom of said plate column to said recovery site, and wherein the ratios: Hi/Hd=50% to 80% and Hr/Hd=0% to 40%.

15. A method of purifying acetic anhydride or a mixture of acetic anhydride and acetic acid as recited in claim 14, wherein said ozone-treated acetic anhydride or said ozone-treated mixture of acetic anhydride and acetic acid is introduced into a plate column, having a top and a bottom and a middle section, at an introduction site located at said middle section of said plate column or at an upper part of said middle section, wherein said plate column contains 20 to 80 plates, and wherein a low-boiling impurity fraction is partly recovered from said top of said plate column, and wherein remaining overhead liquid is returned to said top of said plate column as a reflux, and wherein purified anhydride or a purified mixture of acetic anhydride and acetic acid is recovered in a vapor form from said 1st to 5th plate from said bottom of said plate column, with a high-boiling impurity fraction being recovered from said bottom of said plate column.

16. A method of purifying acetic anhydride or a mixture of acetic anhydride and acetic acid as claimed in claim 15, wherein said plate column is operated at a reflux ratio of 50 to 500.

17. A method of purifying acetic anhydride or a mixture of acetic anhydride and acetic acid containing methyl crotonate, vinyl acetate, or both as impurities, wherein said acetic anhydride or said mixture of acetic anhydride and acetic acid is produced by reacting (1) dimethyl ether, (2) methyl acetate, (3) a mixture of dimethyl ether and methanol, (4) a mixture of methyl acetate and methanol, or (5) a mixture of dimethyl ether, methyl acetate and methanol with carbon monoxide, which comprises the steps of:

contacting said acetic anhydride or said mixture of acetic anhydride and acetic acid with ozone used in an amount, on a molar basis, 1.1 to 1.7 times the carbon-carbon double bond in said impurities at a temperature of 20° C. to 35° C. to attain an average contact time of 1 to 30 minutes;

introducing said ozone-treated acetic anhydride or said ozone-treated mixture of acetic anhydride and acetic acid into a plate column, having a top and a bottom and a middle section, at an introduction site located at said middle section of said plate column or at an upper part of said middle section, wherein said plate column contains 20 to 80 trays and is operated at a column top pressure of 100 mmHg to atmospheric pressure;

partly recovering a low-boiling impurity fraction from said top of said plate column and returning remaining overhead liquid to said top of said plate column as a reflux in a reflux ratio of 50 to 500; and recovering purified acetic anhydride or purified mixture in a vapor or liquid form from a recovery site located from said 1st to 5th plate from said bottom of said plate column, with a high-boiling impurity fraction being recovered from said bottom of said plate column.

* * * * *